US008251064B2

(12) United States Patent
Sanders

(10) Patent No.: US 8,251,064 B2
(45) Date of Patent: Aug. 28, 2012

(54) ARTICULATED FIREFIGHTER BREATHING PACK

(76) Inventor: Stan A. Sanders, Chesterfield, MO (US)

( * ) Notice: Subject to any disclaimer, the term of this patent is extended or adjusted under 35 U.S.C. 154(b) by 329 days.

(21) Appl. No.: 12/707,287

(22) Filed: Feb. 17, 2010

(65) Prior Publication Data

US 2011/0197891 A1 Aug. 18, 2011

(51) Int. Cl.
*A61M 11/00* (2006.01)

(52) U.S. Cl. .................. 128/205.22; 128/202.19; 2/458; 224/606; 220/581; 206/0.6

(58) Field of Classification Search ............. 128/202.19, 128/202.13, 205.22; 2/458, 93, 81; 224/606, 224/660, 205.22; 220/581, 592; 206/0.6
See application file for complete search history.

(56) References Cited

U.S. PATENT DOCUMENTS 4,062,356 A 12/1977 Merrifield
4,722,333 A * 2/1988 Bartos ...................... 128/202.27
4,964,405 A 10/1990 Arnoth
5,127,399 A 7/1992 Scholley
5,188,267 A * 2/1993 Sargent et al. ...................... 2/95
6,047,860 A 4/2000 Sanders
6,227,199 B1 5/2001 Garofalo
6,502,571 B1 1/2003 Izuchukwu et al.
6,510,849 B1 1/2003 Izuchukwu et al.
6,513,522 B1 2/2003 Izuchukwu et al.
6,513,523 B1 2/2003 Izuchukwu et al.
6,526,968 B1 3/2003 Izuchukwu et al.
6,579,401 B1 6/2003 Izuchukwu et al.
6,651,659 B2 11/2003 Izuchukwu et al.
7,090,736 B2 8/2006 Le Breton
7,124,908 B2 10/2006 Sanders
7,156,094 B2 1/2007 Chornyj
7,380,551 B2 * 6/2008 Alvey ...................... 128/201.25
8,113,198 B2 * 2/2012 Teetzel et al. ............ 128/205.12
2002/0153009 A1 10/2002 Chornyj
2008/0267715 A1 10/2008 Sullivan
2009/0229603 A1 * 9/2009 Grilliot et al. ........... 128/202.19
2009/0229613 A1 * 9/2009 Grilliot et al. ........... 128/205.22

* cited by examiner

*Primary Examiner* — Steven Douglas
(74) *Attorney, Agent, or Firm* — David A. Belasco; Belasco Jacobs & Townsley, LLP

(57) ABSTRACT

An articulated firefighter breathing pack includes multiple polymeric pressure vessels connected together and to a flexible manifold with sections of flexible conduit. The pressure vessels and sections of flexible conduit are encased in high strength fiber material. The pressure vessels are wrapped in high strength ballistic ribbon material. The manifold provides connections for a high pressure regulator and an air fill source. A low pressure hose is connected to the high pressure regulator, a low pressure regulator is connected to the low pressure hose and a mouthpiece connected to the low pressure regulator. A pressure vessel container attaches the pressure vessels, the flexible conduit and the manifold to a harness having a waist portion and two vertical straps extending upwardly over the shoulders and back down to the waist portion. A utility belt provides mounting for equipment for the breathing pack including hoses, a power supply, electronic sensors and controls.

26 Claims, 15 Drawing Sheets

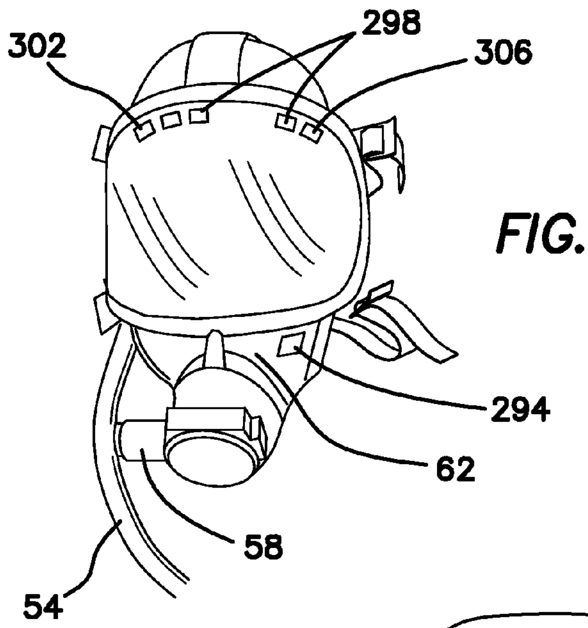
FIG. 3
FIG. 4
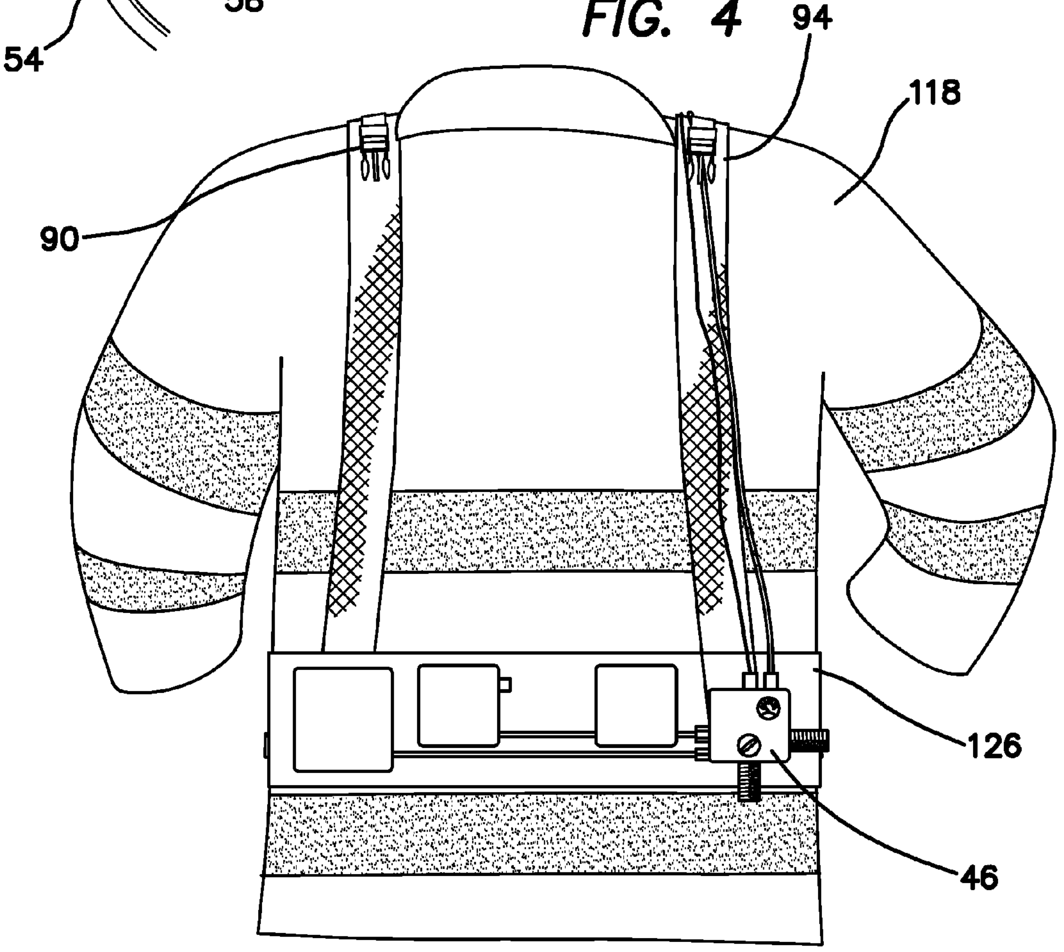

FIG. 7
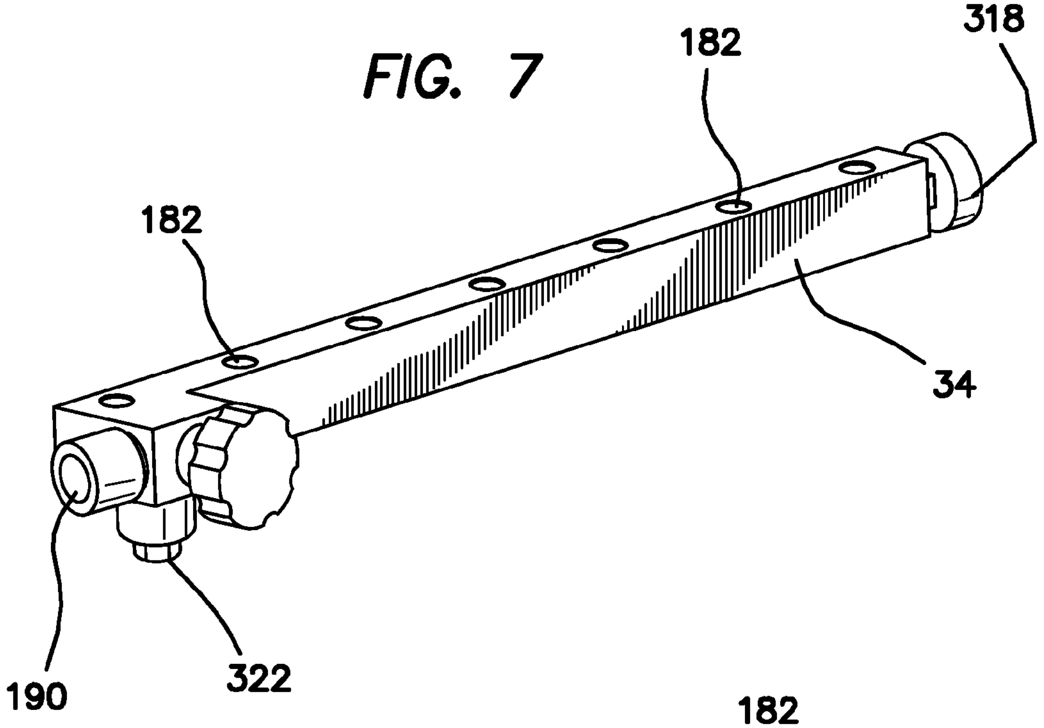
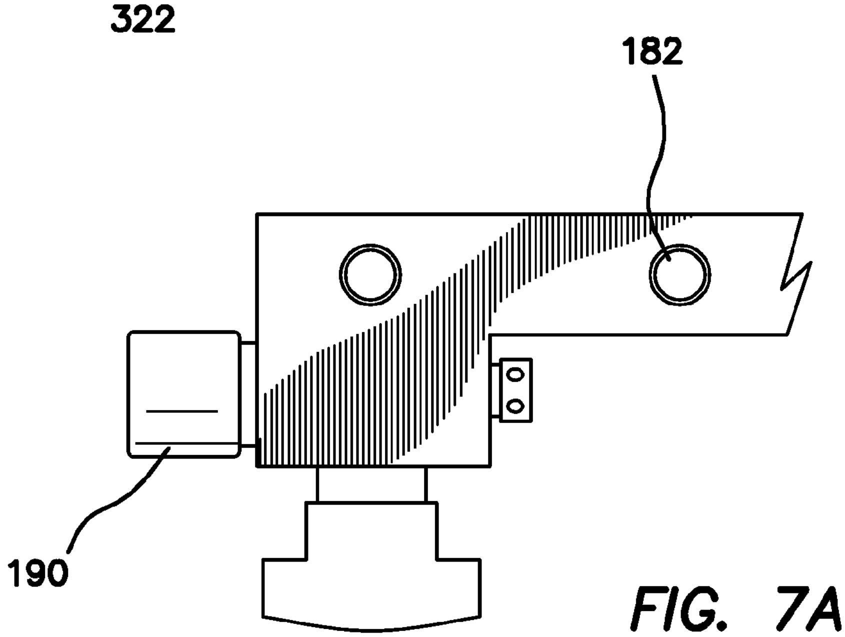
FIG. 7A

ARTICULATED FIREFIGHTER BREATHING PACK

FIELD OF INVENTION

This invention relates to the field of portable breathing systems, and more specifically to breathing apparatus designed for use by firefighters.

BACKGROUND OF THE INVENTION

Firefighters regularly enter burning buildings to rescue persons and to protect property. These buildings usually contain large quantities of smoke and/or other gaseous toxic substances. In order to protect the firefighters from such harmful substances, portable breathing devices have been developed. Typically, these breathing devices comprise a high pressure metallic cylinder, a backpack for mounting the cylinder, a first stage regulator attached to the cylinder, a low pressure hose and a second stage regulator attached to a mouth piece. Devices such as this are relatively heavy and bulky. Such systems are potentially dangerous for the firefighter as they can easily snag on building features found in burning and collapsing structures. Further, because of the use of traditional metallic pressure cylinders, such breathing packs are quite heavy, causing undue fatigue to firefighters. Even worse, such pressure cylinders can explode if subjected to excessive heat, should their overpressure safety devices fail. Current designs for firefighter breathing packs are also rigid and uncomfortable for the firefighter to wear as they do not conform to the back of the firefighter. A variety of designs for firefighter packs and the pressure vessels that they require have been developed to address these issues.

U.S. Pat. No. 7,156,094, issued to Chornyj, is directed to a breathing apparatus and pressure vessels therefore. The apparatus is a self-contained vest that is worn by a user and has pressurized cylinders or flasks of breathable air distributed around the garment. The vest may be utilized in a number of situations, including firefighting, or in other hazardous environments where emergency air supply is required. The vest uses a series of interconnected high pressure vessels which are made of a carbon fiber epoxy with a rubber or nylon coating on their inner surface, and a rubber or nylon coating on their outer surface. In order to strengthen the vessels, an over-wrapped layer may be wound around the cord that is made of a carbon composite thread such as Kevlar®. The vessel may be contained within a bag that is made of braided stainless steel cable to resemble a fish net. The vest includes a series of vessels which are interconnected with a series of first stage regulators and hoses that connect to a second stage-regulator on the vest front. The vest may be made of a fire resistant material so that the device may be used in a firefighting clothing situation. High pressure cylinders or flasks are contained within pockets on the vest garment but the design of the device maintains flexibility to provide comfort and ease of use for the user. A combination high-pressure shut-off valve and first stage regulator with a low pressure valve are attached to each cylinder or flask.

U.S. Pat. No. 6,513,522, issued to Izuchukwu et al. is directed to a wearable storage system for pressurized fluids. The pressure vessel is formed from a plurality of polymeric hollow chambers of varying shapes and interconnected by conduit sections between the chambers. The pressure vessels are reinforced by a filament wrapping. A fluid transfer control system is attached to the vessels for controlling the flow thereof. The entire system is incorporated into a wearable garment so that the device is portable and capable of supplying the necessary gas for a patient or other user. An example chamber is depicted as a shell which is molded of a synthetic plastic material that may be welded to another shell by means of an ultrasonic welding device or a radio frequency energy device. The exterior of the shells are wrapped with pressure resistant filaments with a protective synthetic plastic coating that also may be applied. The shells may be either blow molded or injection molded, and various materials such as Teflon or fluorinated ethylene may be used. The pressure resistant filaments may be made of a carbon fiber such as Kevlar®. The inlet of the tubular core may be fitted with a suitable threaded male fitting, whereas the rear end of the core may be provided with a threaded fitting in order to close off the end. These fittings may also be used to incorporate valves or gages. Individual chambers are pneumatically interconnected by means of conduit sections of varying lengths.

U.S. Pat. No. 5,127,399, issued to Scholley is directed to a flexible container for use with compressed gases, and may be utilized in the form of a garment worn by the user such as a firefighter. The system described provides additional examples of a breathing apparatus for compressed gases and include examples of a pressure regulator, a demand flow regulator, and the use of fiber braids or windings. This reference is directed to a flexible container for use with compressed gases and may be utilized in the form of a garment worn by the user such as a firefighter. The system described in this patent provides additional examples of a breathing apparatus for compressed gases and include examples of a pressure regulator, a demand flow regulator, and the use of fiber braids or windings.

U.S. Pat. No. 4,964,405, issued to Arnoth is directed to an emergency respiration apparatus and is simply a lightweight self-contained unit that supplies pressurized breathable gas to be incorporated into a vest or other garment for use in hazardous work areas.

U.S. Pat. No. 6,227,199, issued to Garofalo is directed to a multiple distributor for low-pressure uses to be incorporated into equipment such as a self-contained breathing apparatus. The distributor is connected to a first-stage pressure reducer of the cylinder and fastened or incorporated into a jacket.

It is an objective of the present invention to provide a compact, articulated portable breathing system for use by firefighters. It is a further objective to provide such a system that is light weight and conforms to the back of the firefighter. It is a still further objective of the invention to use polymeric pressure vessels that will not explode when exposed to heat. It is yet a further objective to provide pressure vessels that will dissipate pressure in a controlled manner. It is another objective of the present invention to provide a vessel manifold that conforms to the firefighter's back for maximum comfort. Finally, it is an objective to provide a system that can be rapidly filled, is durable, and is inexpensive to produce.

While some of the objectives of the present invention are disclosed in the prior art, none of the inventions found include all of the requirements identified.

SUMMARY OF THE INVENTION

The present invention addresses all of the deficiencies of prior art articulated firefighter breathing pack inventions and satisfies all of the objectives described above.

(1) An articulated firefighter breathing pack providing the desired features may be constructed from the following components. A plurality of polymeric pressure vessels is provided. Each of the vessels has an elongated cylindrical shape, a first end and a second end. Each of the first and second ends has an attached section of flexible conduit. Each of the sections of flexible conduit is attached to either a sealing fitting, another section of flexible conduit attached to another vessel or a manifold. Each of the pressure vessels is attached to at least one other pressure vessel with one of the sections of flexible conduit. The pressure vessels and the sections of flexible conduit are encased in high strength fiber material. The pressure vessels are wrapped with a high strength ballistic ribbon material. A manifold is provided. The manifold is connected to a plurality of sections of flexible conduit connected to the pressure vessels. The manifold provides connections for a high pressure regulator and an air fill source. A high pressure regulator is provided, as is a low pressure hose connected to the high pressure regulator. A low pressure regulator is connected to the low pressure hose and a mouthpiece is connected to the low pressure regulator. A high pressure regulator manages vessel pressure ranging from approximately 0-6000 psi. Low pressure regulator manage pressures of approximately 100-150 psi. A pressure vessel container is provided. The container is formed of flexible, fireproof material and is sized and shaped to accommodate the plurality of pressure vessels, the sections of flexible conduit and the manifold. The container has a closable opening for introduction and removal of the pressure vessels, the sections of flexible conduit and the manifold. The container has openings sized and shaped to accommodate passage of at least one low pressure hose and for connection to the air fill source. The container has means for removably attaching to a harness. A harness is provided. The harness is formed of flexible, fireproof material and includes a waist portion that has a fastener, a front portion extending upwardly from the waist portion and connecting to a back portion extending downwardly to the waist portion. The back portion has means for removably attaching to the pressure vessel container.

The harness is worn over an outer garment of a firefighter, the pressure vessel container is attached to the harness, the manifold is connected to the high pressure regulator, the pressure vessels are filled with air through the connection to the air fill source, rendering the breathing pack ready for use by a firefighter.

(2) In a variant of the invention, a utility belt is provided. The utility belt has mounting means for accommodating equipment for said breathing pack, a closure means and is worn either under or over the harness.

(3) In another variant, the utility belt includes a second low pressure hose, a portable power source, breathing pack electronics and mounting means for said high pressure regulator.

(4) In still another variant, the back portion of the harness provides mounting means for accommodating equipment for said breathing pack.

(5) In yet another variant, the back portion of the harness includes a flexible mounting plane, a second low pressure hose, a portable power source, breathing pack electronics and mounting means for said high pressure regulator.

(6) In a further variant, the high strength fiber material is selected from the group consisting of rayon, nylon, glass or Kevlar® (aramid) fiber.

(7) In still a further variant, the high strength ballistic ribbon material is selected from the group consisting of prepreg carbon fiber or prepreg glass fiber.

(8) In another variant, the manifold includes a strip of flexible material. The strip mounts a plurality of connections for the sections of flexible conduit connected to the pressure vessels, a connection for the high pressure regulator and the connection for the air fill source. The flexible strip permits the manifold to conform to a back of a firefighter.

(9) In yet another variant, the manifold includes an integral high pressure regulator.

(10) In a further variant, the high pressure regulator includes a second connection for a low pressure hose. The second connection provides an emergency air source for a second firefighter.

(11) In still a further variant, the high pressure regulator includes a high pressure transfer port. The high pressure transfer port provides an emergency air sharing facility for a second firefighter.

(12) In yet a further variant, the pressure vessel container further includes a closable side opening. The side opening extends from a top end of the container to a point spaced from a bottom end by a first predetermined distance, leaving an unopened side portion. The unopened side portion prevents the pressure vessels and the manifold from falling out of the container should it be left open.

(13) In still another variant, the high pressure regulator is a high pressure transfer block. The high pressure transfer block has a pressure gauge, a fill port with shut off valve, a high pressure connection to the manifold, a high pressure transfer connection for a second firefighter pack, a low pressure connection for a low pressure hose connected to a low pressure regulator 58 and mouthpiece 62, a second low pressure connection 270 for use by a second firefighter, a high pressure connection for a high pressure hose connected to a remote pressure gauge console, and connections for breathing pack electronics.

(14) In yet another variant, the breathing pack electronics include any of a non-breathing alarm, a no motion alarm, a two way radio, a heads-up display providing air level warning lights, and low pressure alarms.

(15) In another variant, the breathing pack electronics include any of a non-breathing alarm, a no motion alarm, a two way radio, a heads-up display providing air level warning lights, and low pressure alarms.

(16) In a further variant, a remote pressure gauge console is provided. The remote pressure gauge console includes an air pressure gauge and alarm activation indicators.

(17) In still a further variant, the articulated firefighter breathing pack includes an air pressure gauge mounted to the manifold.

(18) In yet a further variant, the manifold includes an overpressure rupture fitting.

(19) In another variant of the invention, each of the pressure vessels includes an overpressure rupture fitting.

(20) In still another variant, the polymeric pressure vessels are formed as seamless cylindrical bodies having semi-spherical ends. Each of the ends has a central opening connected to the sections of flexible conduit.

(21) In yet another variant, the polymeric pressure vessels are formed as a pair of two part shells. The shells are welded together and reinforced with a two part ring assembly.

(22) In a further variant, the articulated firefighter breathing pack includes a fireproof cover for the pressure vessels.

(23) In still a further variant of the invention, the fireproof cover includes a pair of mating cover halves. The halves are hingedly attached at a first side edge and detachably fastened at a second side edge.

(24) In yet a further variant, an articulated firefighter breathing pack, includes a plurality of polymeric pressure vessels. Each of the vessels has an elongated cylindrical shape, a first end and a second end. Each of the first and second ends has an attached section of flexible conduit. Each of the sections of flexible conduit is attached to either a sealing fitting, another section of flexible conduit attached to another vessel or a manifold. Each of the pressure vessels is attached to at least one other pressure vessel with one of the sections of flexible conduit. The pressure vessels and the sections of flexible conduit are encased in high strength fiber material. The pressure vessels are wrapped with a high strength ballistic ribbon material.

A manifold is provided. The manifold is connected to a plurality of sections of flexible conduit connected to the pressure vessels. The manifold provides connections for a high pressure regulator and an air fill source. A high pressure regulator is provided. A low pressure hose is connected to the high pressure regulator. A low pressure regulator is connected to the low pressure hose and a mouthpiece is connected to the low pressure regulator. A firefighter turnout coat is provided. The turnout coat is formed of flexible, fireproof material and has a rear pocket. The rear pocket is sized and shaped to accommodate the plurality of pressure vessels, the sections of flexible conduit and the manifold. The rear pocket has a closable upper opening for introduction and removal of the plurality of pressure vessels, the sections of flexible conduit and the manifold. The rear pocket has lower openings for the connections for the high pressure regulator and the air fill source. The turnout coat has front pockets. The front pockets are sized and shaped to contain the high pressure regulator, a portable power source, breathing pack electronics. A front panel of the turnout coat has a mounting point for a gauge console. The plurality of pressure vessels, the sections of flexible conduit and the manifold are placed into the rear pocket of the turnout coat. The manifold is connected to the high pressure regulator, the pressure vessels are filled with air through the connection to the air fill source, rendering the breathing pack ready for use by a firefighter.

(25) In another variant, a high pressure transfer module is provided. The transfer module provides a high pressure connection to a remote pressure gauge console, a high pressure connection to the high pressure regulator, a high pressure transfer connection for a second firefighter pack, a low pressure connection to the high pressure regulator for a low pressure hose connected to the low pressure regulator and the mouthpiece, a second low pressure connection for use by a second firefighter, and connections for breathing pack electronics. The turnout coat has a pocket sized and shaped to removably enclose the high pressure transfer module.

(26) In a final variant of the invention, the breathing pack electronics include any of a non-breathing alarm, a no motion alarm, a two way radio, a heads-up display providing air level warning lights, and low pressure alarms.

An appreciation of the other aims and objectives of the present invention and an understanding of it may be achieved by referring to the accompanying drawings and the detailed description of a preferred embodiment.

DESCRIPTION OF THE DRAWINGS

FIG. 3 is a perspective view of a mouthpiece and face shield of the FIG. 1 embodiment;

FIG. 4 is a rear view of the firefighter's turnout coat with attached harness and utility belt of an alternative embodiment of the invention;

FIG. 7 is a perspective view of a fixed manifold with attached gauge and overpressure rupture fitting;

FIG. 7A is a partial perspective view of a fixed manifold illustrating a connection for an air fill source;

DETAILED DESCRIPTION OF THE PREFERRED EMBODIMENT (1) FIGS. 1-20 illustrate an articulated firefighter breathing pack 10 providing the desired features that may be constructed from the following components. As illustrated in FIG. 1, a plurality of polymeric pressure vessels 14 is provided. Each of the vessels 14 has an elongated cylindrical shape, a first end 18 and a second end 22. Each of the first 18 and second 22 ends has an attached section of flexible conduit 26. Each of the sections of flexible conduit 26 is attached to either a sealing fitting 30, another section of flexible conduit 26 attached to another vessel 14 or a manifold 34. Each of the pressure vessels 14 is attached to at least one other pressure vessel 14 with one of the sections of flexible conduit 26. The pressure vessels 14 and the sections of flexible conduit 26 are encased in high strength fiber material 38. The pressure vessels 14 are wrapped with a high strength ballistic ribbon material 42. A manifold 34 is provided. The manifold 34 is connected to a plurality of sections of flexible conduit 26 connected to the pressure vessels 14. The manifold 34 provides connections 36, 40 for a high pressure regulator 46 and an air fill source (not shown). As illustrated in FIGS. 4 and 5, a high pressure regulator 46 is provided, as is a low pressure hose 54 connected to the high pressure regulator 46. A low pressure regulator 58 is connected to the low pressure hose 54 and a mouthpiece 62 is connected to the low pressure regulator 58. A high pressure regulator 46 manages vessel pressure ranging from approximately 0-6000 psi. Low pressure regulator 58 manage pressures of approximately 100-150 psi.

Figure 1:
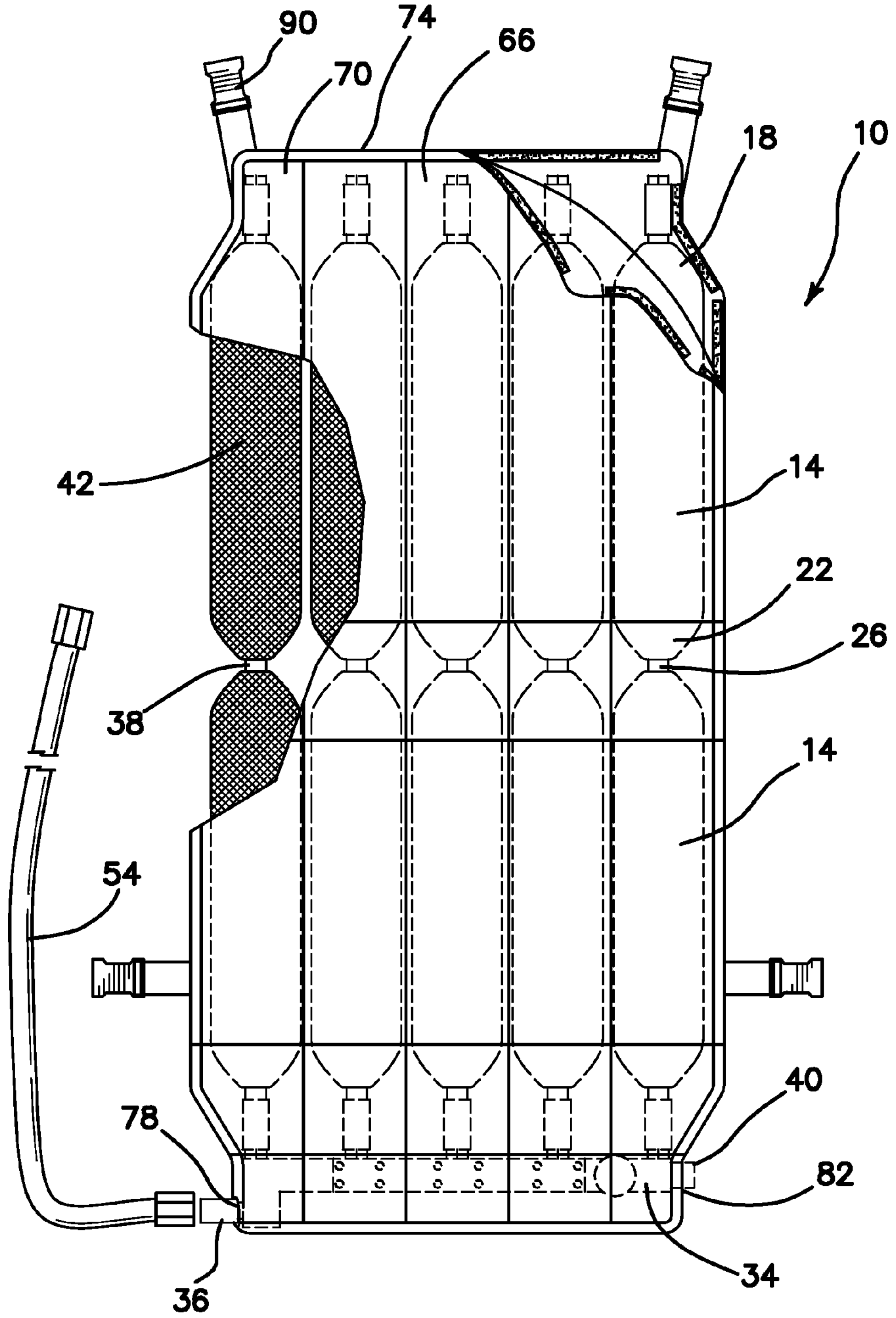
FIG. 1 is a partially cut-away side elevational view of the preferred embodiment of the invention illustrating the flexibly joined pressure vessels, manifold, pressure vessel container and low pressure hose.
Figure 2:
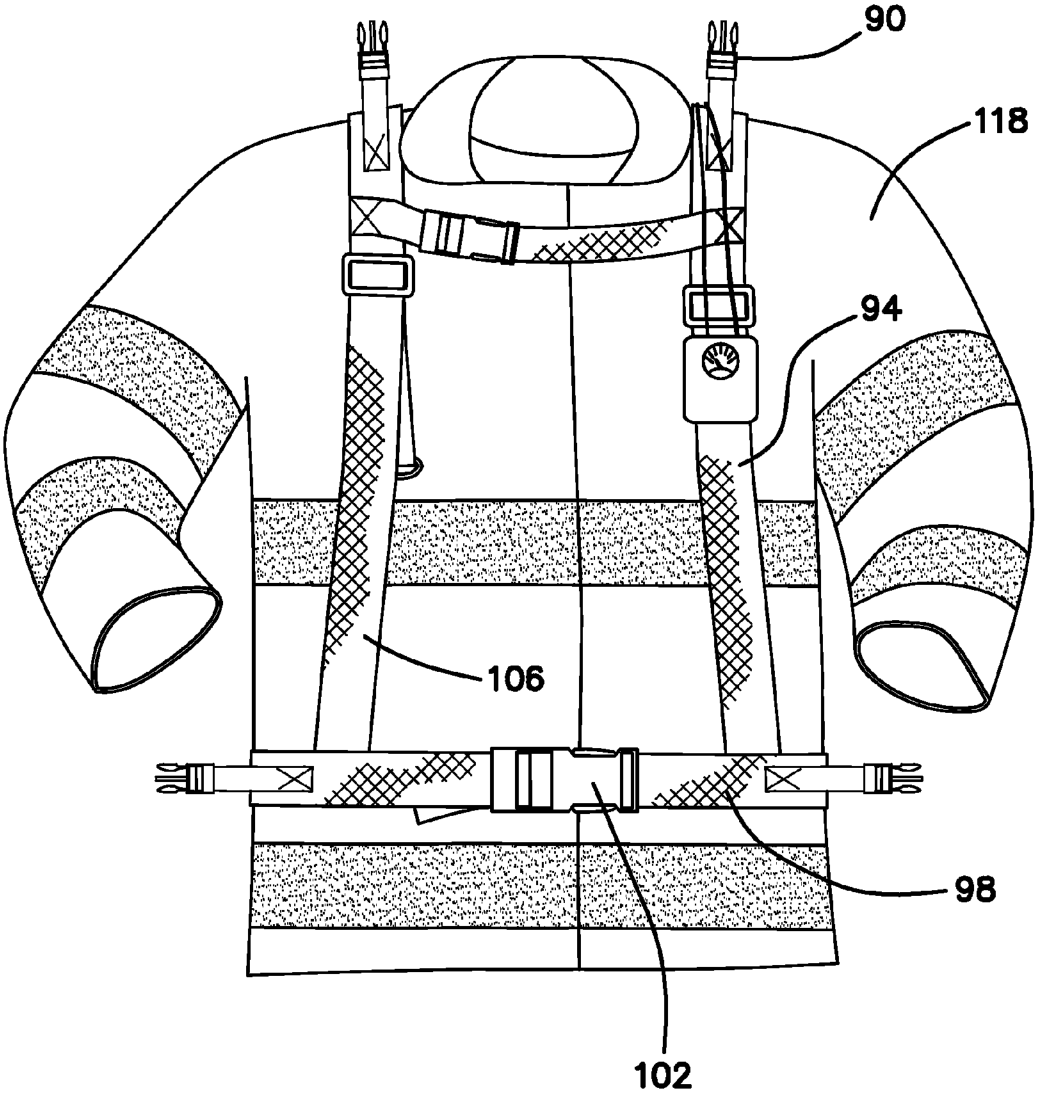
FIG. 2 is a front view of a firefighter's turnout coat with attached harness and gauge console of the FIG. 1 embodiment.

As illustrated in FIG. 1, a pressure vessel container 66 is provided. The container 66 is formed of flexible, fireproof material 70 and is sized and shaped to accommodate the plurality of pressure vessels 14, the sections of flexible conduit 26 and the manifold 34. The container 66 has a closable opening 74 for introduction and removal of the pressure vessels 14, the sections of flexible conduit 26 and the manifold 34. The container 66 has openings 78, 82 sized and shaped to accommodate passage of at least one low pressure hose 54 and for connection to the air fill source. The container has means 90 for removably attaching to a harness 94. As illustrated in FIGS. 2, 4, 6 and 11, a harness 94 is provided. The harness 94 includes a waist portion 98 that has a fastener 102, a front portion 106 extending upwardly from the waist portion 98 and connecting to a back portion 114 extending downwardly to the waist portion 98. The back portion 114 has means 90 for removably attaching to the pressure vessel container 66.

The harness 94 is worn over an outer garment 118 of a firefighter (not shown), the pressure vessel container 66 is attached to the harness 94, the manifold 34 is connected to the high pressure regulator 46, the pressure vessels 14 are filled with air through the connection to the air fill source, rendering the breathing pack 10 ready for use by a firefighter.

Figure 5:
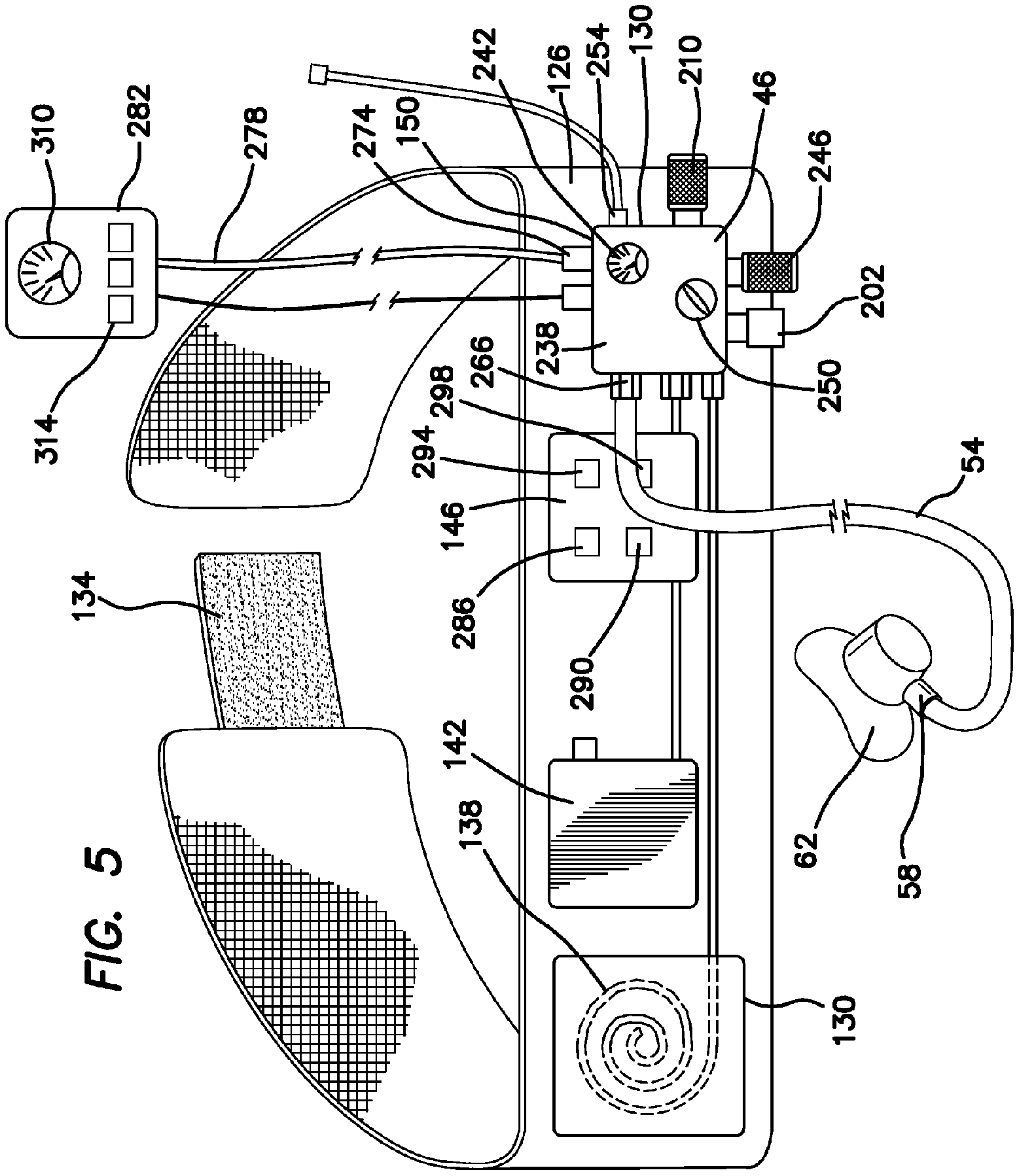
FIG. 5 is a detailed view of the utility belt of the FIG. 4 embodiment, illustrating a high pressure regulator, portable power source, breathing pack electronics, second low pressure hose and attachments for the gauge console and alarms.
Figure 6:
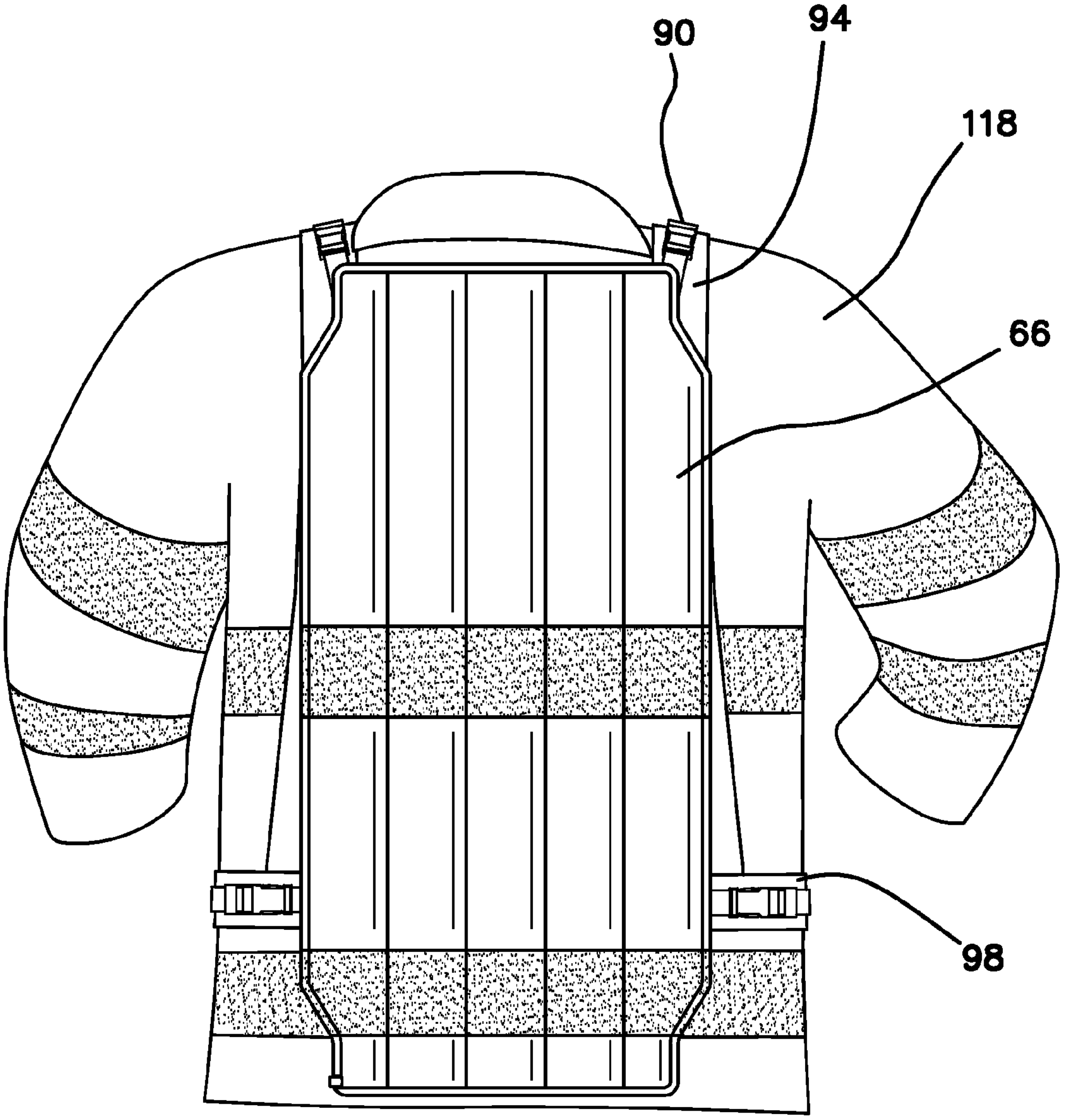
FIG. 6 is rear view of the firefighter's turnout coat with the pressure vessel container attached to the harness.

(2) In a variant of the invention, as illustrated in FIGS. 4 and 5, a utility belt 126 is provided. The utility belt 126 has mounting means 130 for accommodating equipment for said breathing pack 10, a closure means 134 and is worn either under or over the harness 94.

(3) In another variant, the utility belt 126 includes a second low pressure hose 138, a portable power source 142, breathing pack electronics 146 and mounting means 150 for said high pressure regulator 46.

Figure 11:
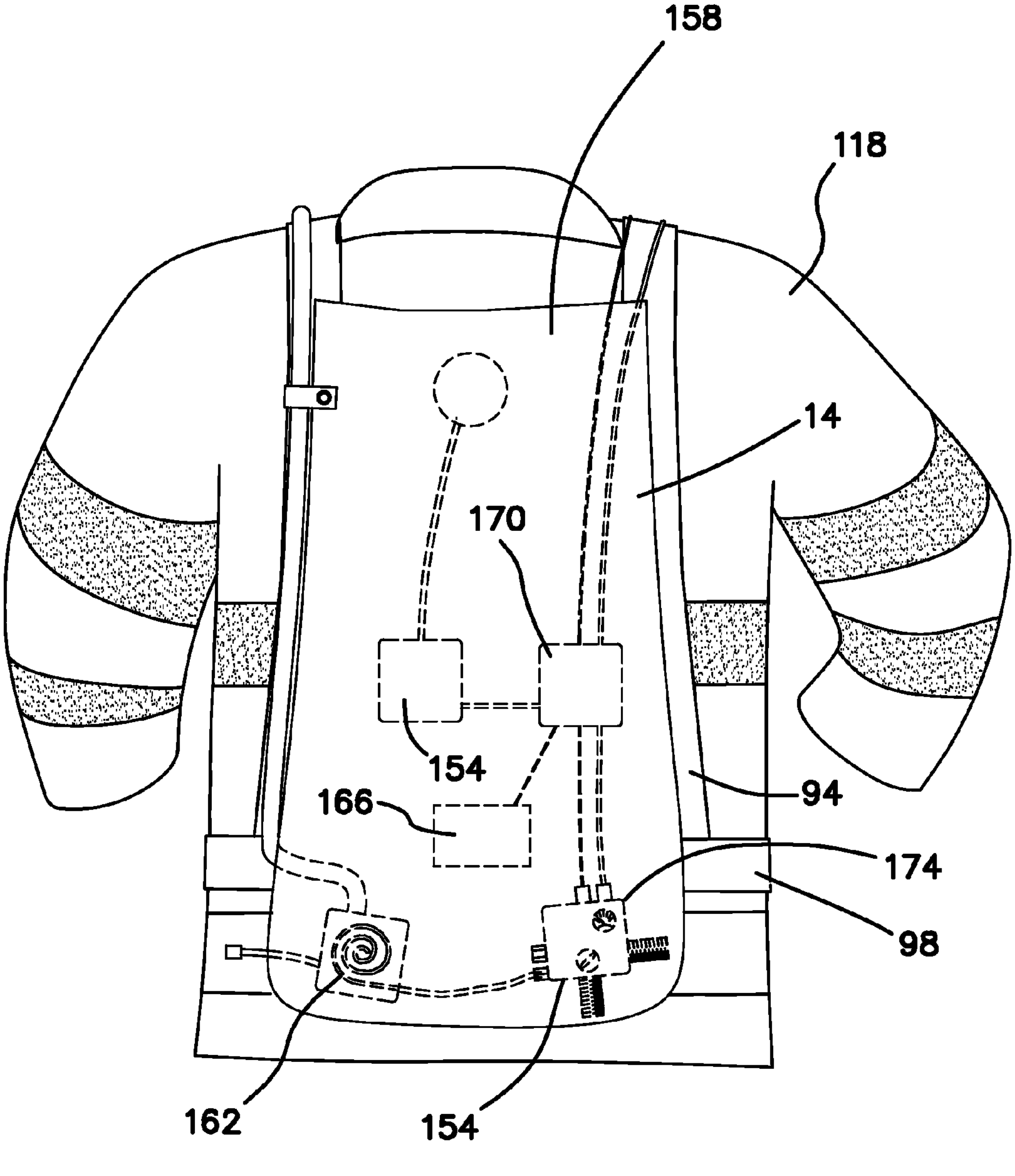
FIG. 11 is a rear view of a firefighter's turnout coat with an alternative embodiment of an attached harness with an integral container for the hardware and electronics for the breathing pack.

(4) In still another variant, as illustrated in FIG. 11, the back portion 114 of the harness 94 provides mounting means 154 for accommodating equipment for said breathing pack 10.

(5) In yet another variant, the back portion 114 of the harness 94 includes a flexible mounting plane 158, a second low pressure hose 162, a portable power source 166, breathing pack electronics 170 and mounting means 174 for said high pressure regulator 46.

(6) In a further variant, the high strength fiber material 38 is selected from the group consisting of rayon, nylon, glass or Kevlar® fiber (aramid).

(7) In still a further variant, the high strength ballistic ribbon material 42 is selected from the group consisting of prepreg carbon fiber or prepreg glass fiber.

Figure 8:
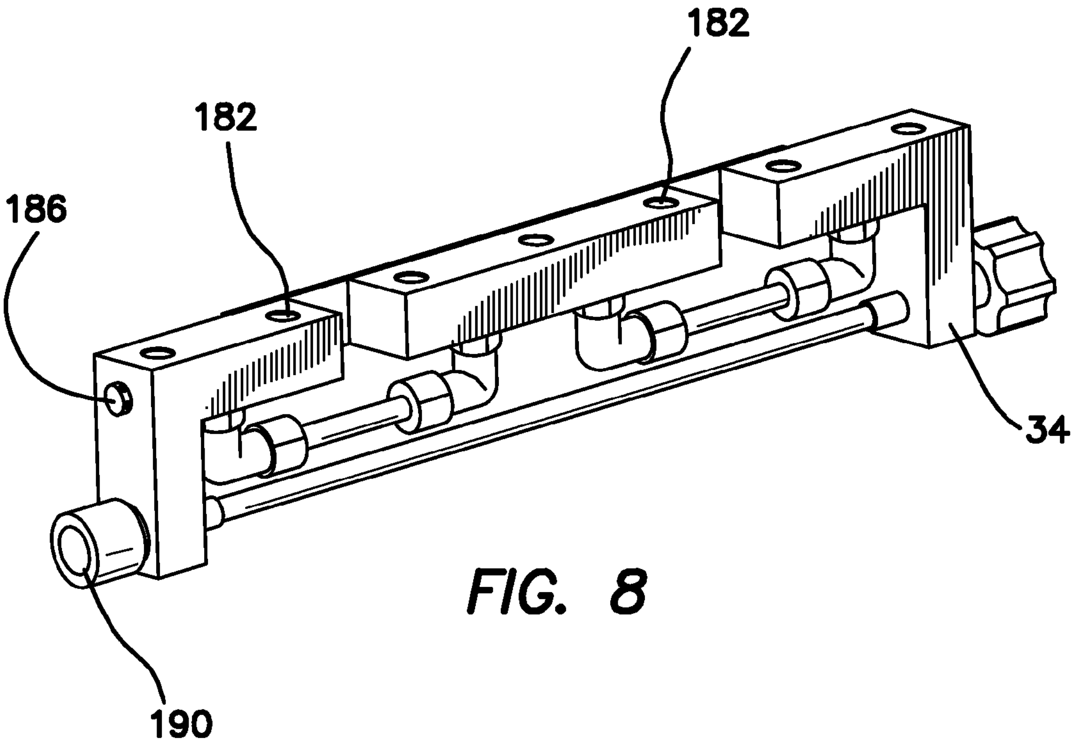
FIG. 8 is a perspective view of a flexible manifold having a connection for a high pressure regulator.
Figure 9:
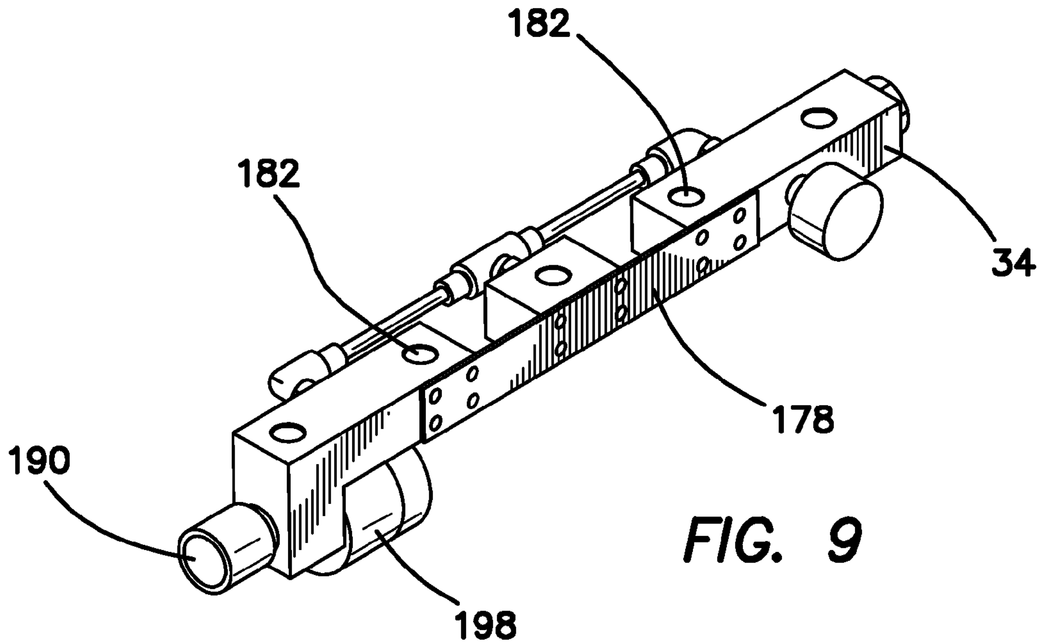
FIG. 9 is a perspective view of a flexible manifold having an integral high pressure regulator.

(8) In still another variant, as illustrated in FIGS. 7-9, the manifold 34 includes a strip of flexible material 178. The strip 178 mounts a plurality of connections 182 for the sections of flexible conduit 26 connected to the pressure vessels 14, a connection 186 for the high pressure regulator 46 and the connection 190 for the air fill source. The flexible strip 178 permits the manifold 34 to conform to a back (not shown) of a firefighter.

(9) In yet another variant, as illustrated in FIG. 9, the manifold 34 includes an integral high pressure regulator 198.

(10) In a further variant, as illustrated in FIG. 5, the high pressure regulator 46 includes a second connection 202 for a low pressure hose 54. The second connection 202 provides an emergency air source for a second firefighter (not shown).

(11) In still a further variant, the high pressure regulator 46 includes a high pressure transfer port 210. The high pressure transfer port 210 provides an emergency air sharing facility for a second firefighter.

(12) In yet a further variant, as illustrated in FIG. 1, the pressure vessel container 66 further includes a closable side opening 214. The side opening 214 extends from a top end 218 of the container 66 to a point 222 spaced from a bottom end 226 by a first predetermined distance 230, leaving an unopened side portion 234. The unopened side portion 234 prevents the pressure vessels 14 and the manifold 34 from falling out of the container 66 should it be left open.

(13) In still another variant, as illustrated in FIGS. 4 and 5, the high pressure regulator 46 is a high pressure transfer block 238. The high pressure transfer block 238 has a pressure gauge 242, a fill port 246 with shut off valve 250, a high pressure connection 254 to the manifold 34, a high pressure transfer connection 210 for a second firefighter pack (not shown), a low pressure connection 266 for a low pressure hose 54 connected to a low pressure regulator 58 and mouthpiece 62, a second low pressure connection 202 for use by a second firefighter, a high pressure connection 274 for a high pressure hose 278 connected to a remote pressure gauge console 282, and connections for breathing pack electronics 146.

(14) In yet another variant, as illustrated in FIGS. 3 and 4, the breathing pack electronics 146 include any of a non-breathing alarm 286, a no motion alarm 290, a two way radio 294, a heads-up display 298 providing air level warning lights 302, and low pressure alarms 306.

(15) In another variant, the breathing pack electronics 146 include any of a non-breathing alarm 286, a no motion alarm 290, a two way radio 294, a heads-up display 298 providing air level warning lights 302, and low pressure alarms 306.

(16) In a further variant, as illustrated in FIG. 5, a remote pressure gauge console 282 is provided. The remote pressure gauge console 282 includes an air pressure gauge 310 and alarm activation indicators 314.

(17) In still a further variant, as illustrated in FIG. 7, the articulated firefighter breathing pack 10 includes an air pressure gauge 318 mounted to the manifold 34.

(18) In yet a further variant, the manifold 34 includes an overpressure rupture fitting 322.

Figure 10:
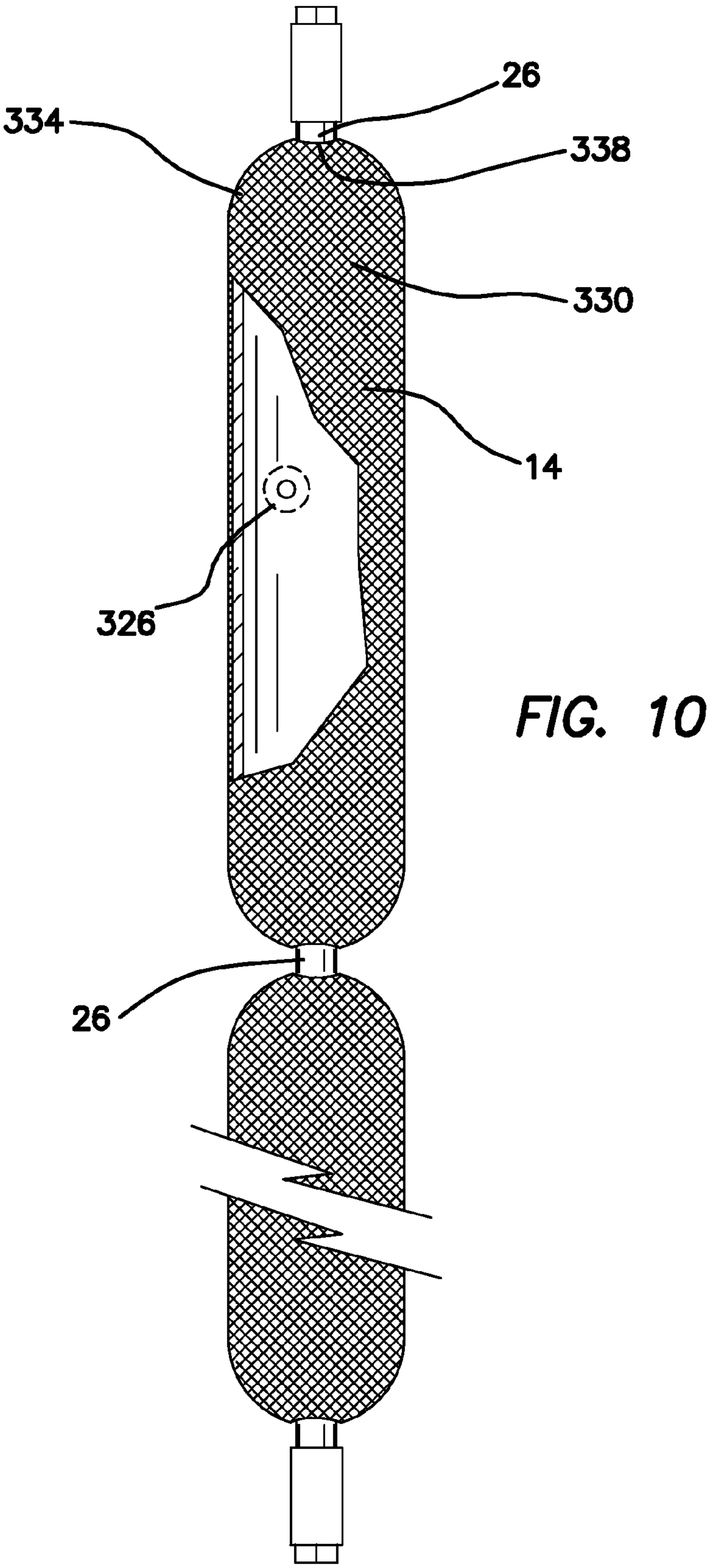
FIG. 10 is a partial cut-away side elevational view of two flexibly joined pressure vessels illustrating an overpressure rupture fitting.

(19) In another variant of the invention, as illustrated in FIG. 10, each of the pressure vessels 14 includes an overpressure rupture fitting 326.

(20) In still another variant, the polymeric pressure vessels 14 are formed as seamless cylindrical bodies 330 having semi-spherical ends 334. Each of the ends 334 has a central opening 338 connected to the sections of flexible conduit 26.

(21) In yet another variant, as illustrated in FIGS. 13-17, the polymeric pressure vessels 14 are formed as a pair of two part shells 342. The shells 342 are welded together and reinforced with a two part ring assembly 346.

Figure 12:
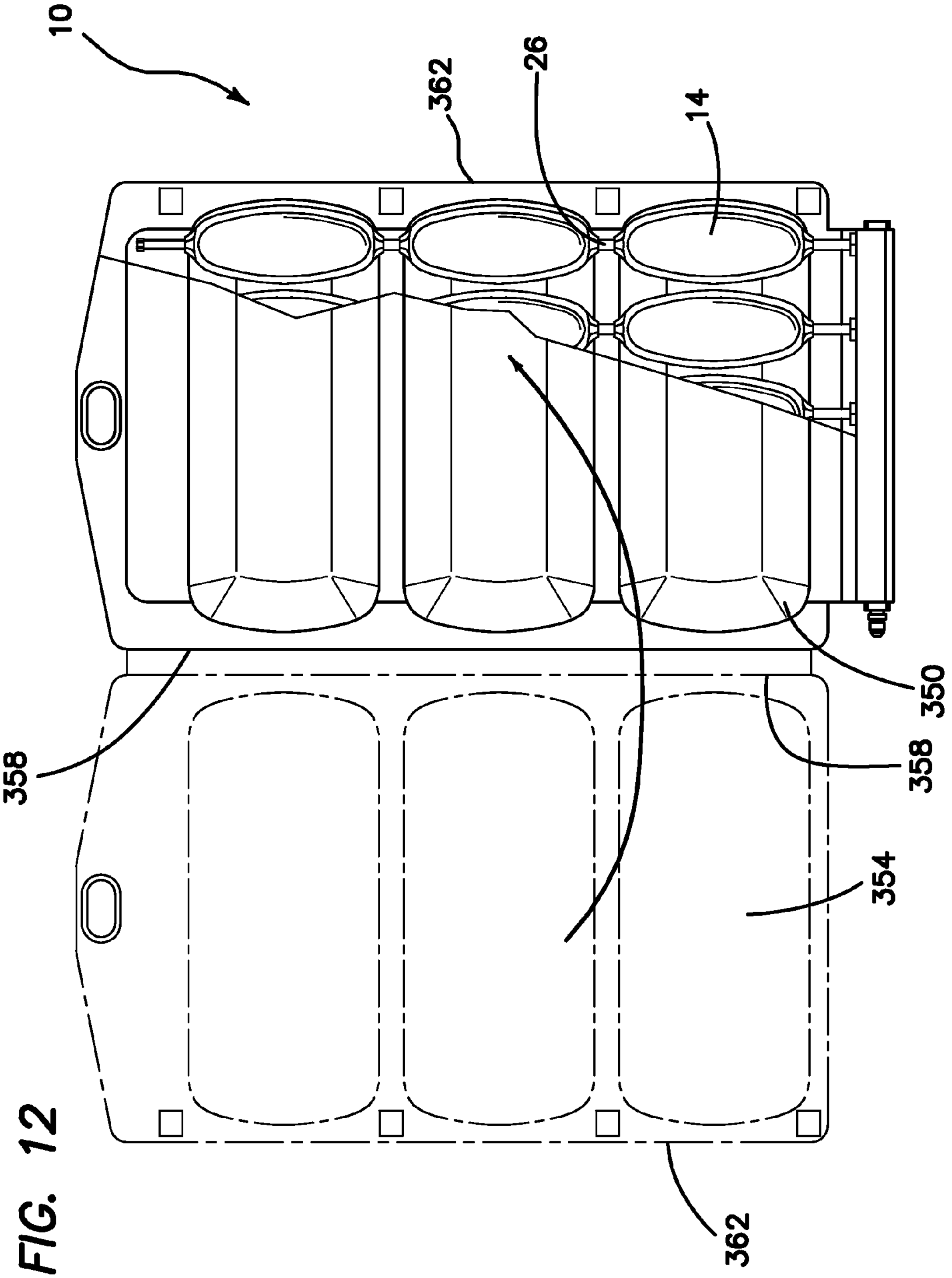
FIG. 12 is a partially cut-away side elevational view of a triple pressure vessel embodiment of the invention disposed within a hinged fireproof cover.
Figure 13:
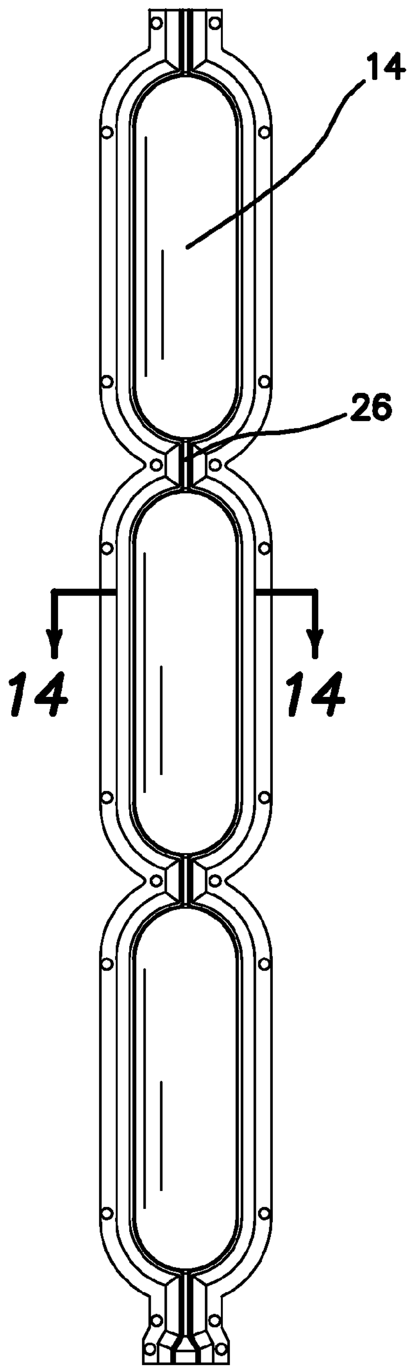
FIG. 13 is a side elevational view of a plurality of two part pressure vessel halves prior to welding.
Figure 17:
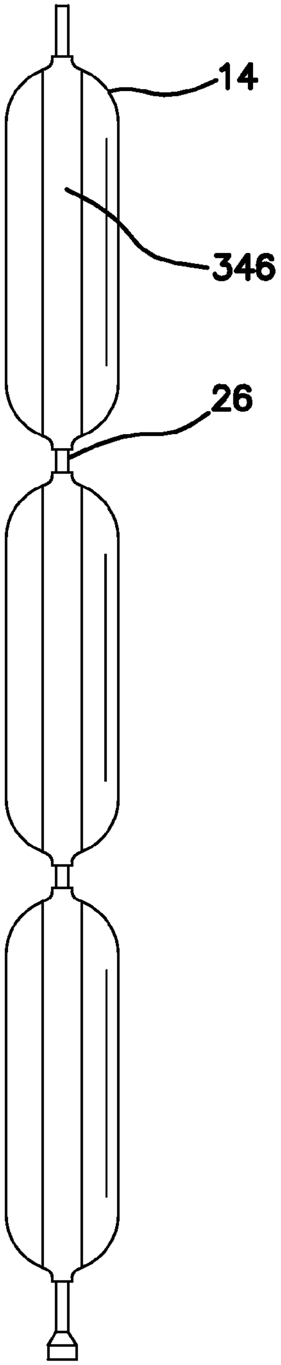
FIG. 17 is a side elavational view of the FIG. 13 pressure vessels with two part ring assembly attached.
Figure 14:
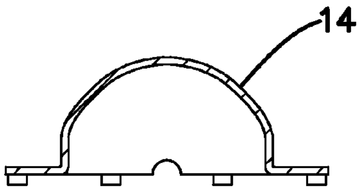
FIG. 14 is a cross-sectional view of the FIG. 13 pressure vessel taken along the line 14-14.
Figure 15:
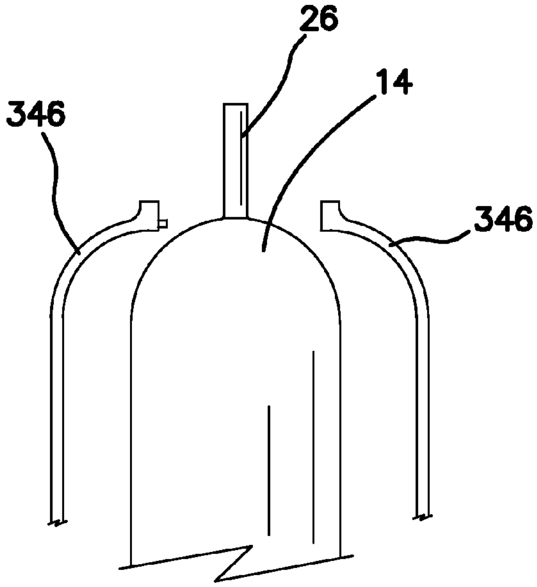
FIG. 15 is a partial plan view of the FIG. 13 pressure vessel with two part ring assembly prior to attachment of the assembly.
Figure 16:
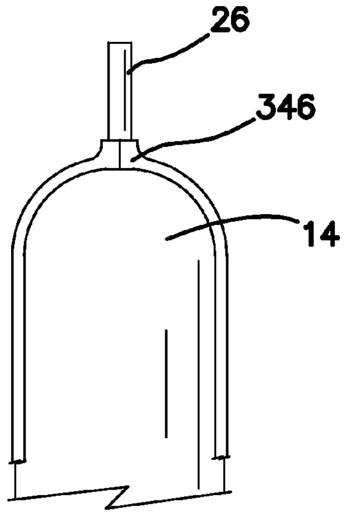
FIG. 16 is a partial plan view of the FIG. 13 pressure vessel with two part ring assembly after attachment of the assembly.

(22) In a further variant, as illustrated in FIG. 12, the articulated firefighter breathing pack 10 includes a fireproof cover 350 for the pressure vessels 14.

(23) In still a further variant of the invention, as illustrated in FIG. 12, the fireproof cover 350 includes a pair of mating cover halves 354. The halves 354 are hingedly attached at a first side edge 358 and detachably fastened at a second side edge 362.

(24) In yet a further variant, as illustrated in FIG. 1, an articulated firefighter breathing pack 10, includes a plurality of polymeric pressure vessels 14. Each of the vessels 14 has an elongated cylindrical shape, a first end 18 and a second end 22. Each of the first 18 and second 22 ends has an attached section of flexible conduit 26. Each of the sections of flexible conduit 26 is attached to either a sealing fitting 30, another section of flexible conduit 26 attached to another vessel 14 or a manifold 34. Each of the pressure vessels 14 is attached to at least one other pressure vessel 14 with one of the sections of flexible conduit 26. The pressure vessels 14 and the sections of flexible conduit 26 are encased in high strength fiber material 38. The pressure vessels 14 are wrapped with a high strength ballistic ribbon material 42.

Figure 18:
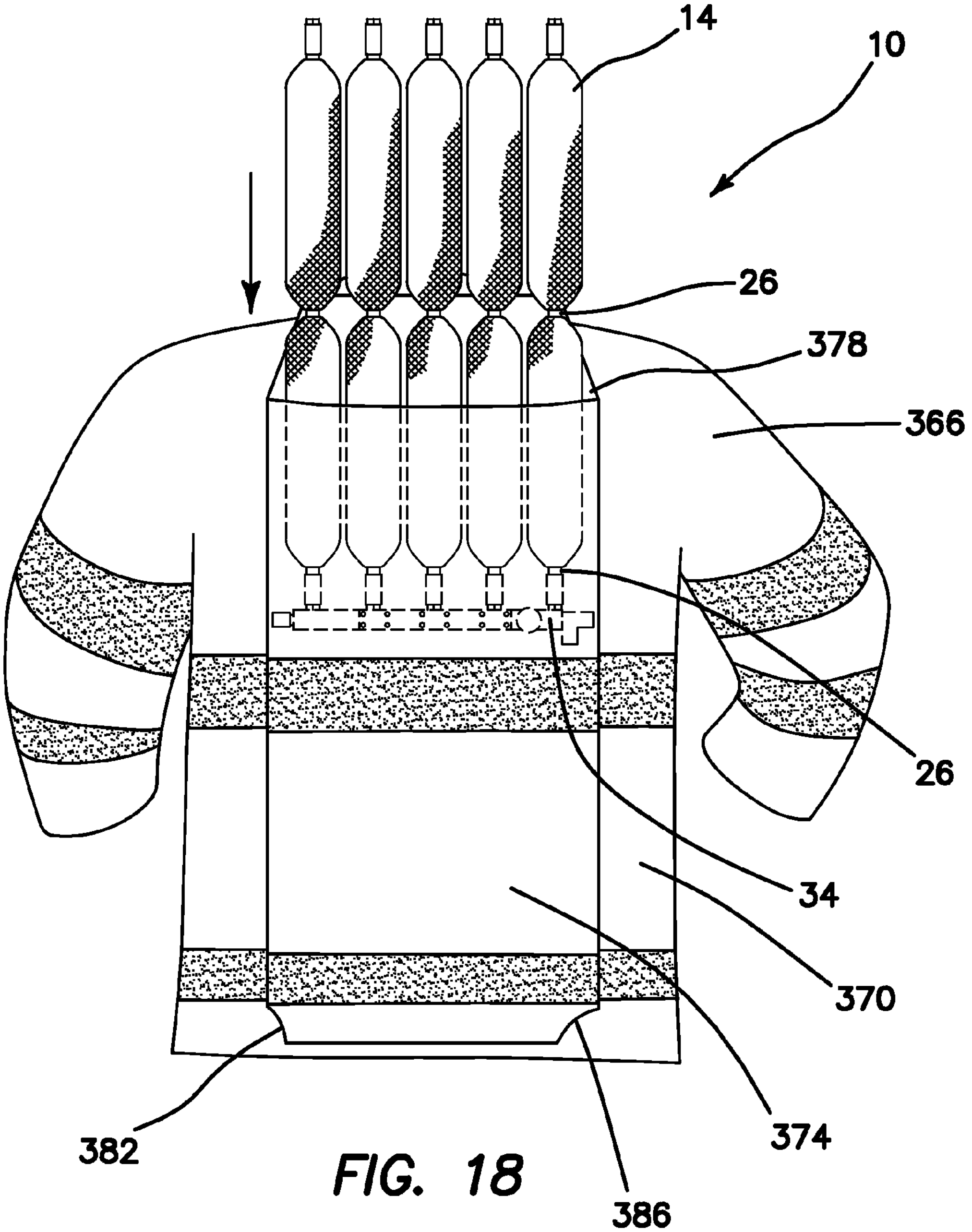
FIG. 18 is a rear view of a turnout coat with integrated pockets showing the loading of the flexibly joined pressure vessels and manifold into the rear pocket.
Figure 19:
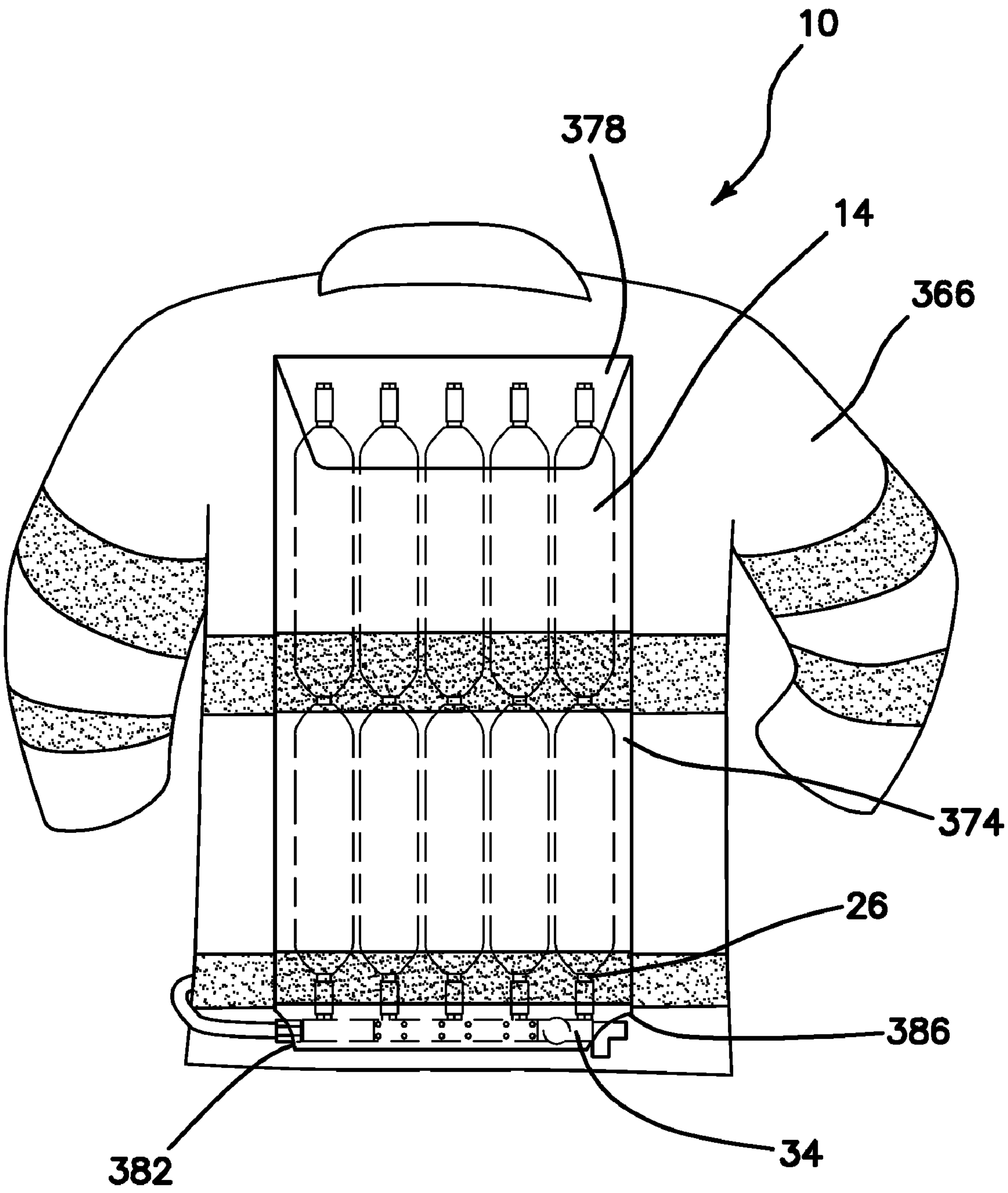
FIG. 19 is a rear view of a turnout coat with integrated pockets showing the flexibly joined pressure vessels and manifold in the closed rear pocket.
Figure 20:
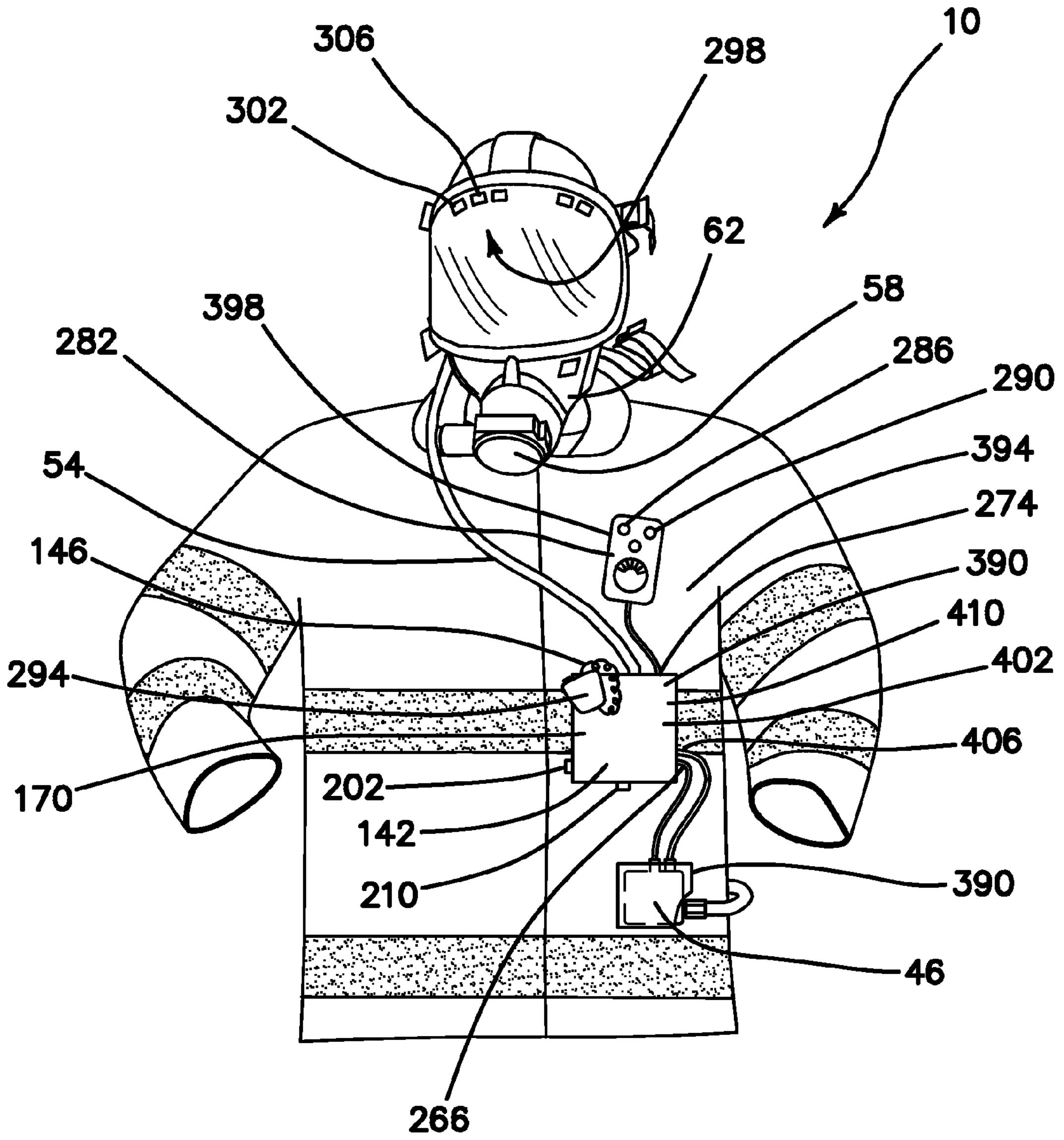
FIG. 20 is a rear view of a turnout coat with integrated pockets illustrating a high pressure transfer module and connections to the manifold and high and low pressure regulators.

A manifold 34 is provided. The manifold 34 is connected to a plurality of sections of flexible conduit 26 connected to the pressure vessels 14. The manifold 34 provides connections 36, 40 for a high pressure regulator 46 and an air fill source (not shown). A high pressure regulator 46 is provided. A low pressure hose 54 is connected to the high pressure regulator 46. A low pressure regulator 58 is connected to the low pressure hose 54 and a mouthpiece 62 is connected to the low pressure regulator 58. As illustrated in FIGS. 18 and 19, a firefighter turnout coat 366 is provided. The turnout coat 366 is formed of flexible, fireproof material 370 and has a rear pocket 374. The rear pocket 374 is sized and shaped to accommodate the plurality of pressure vessels 14, the sections of flexible conduit 26 and the manifold 34. The rear pocket 374 has a closable upper opening 378 for introduction and removal of the plurality of pressure vessels 14, the sections of flexible conduit 26 and the manifold 34. The rear pocket 374 has lower openings 382, 386 for the connections for the high pressure regulator 46 and the air fill source. As illustrated in FIG. 20, the turnout coat 366 has front pockets 390. The front pockets 390 are sized and shaped to contain the high pressure regulator 46, a portable power source 142 and breathing pack electronics 170. A front panel 394 of the turnout coat 366 has a mounting point 398 for a gauge console 282. The plurality of pressure vessels 14, the sections of flexible conduit 26 and the manifold 34 are placed into the rear pocket 374 of the turnout coat 366. The manifold 34 is connected to the high pressure regulator 46, the pressure vessels 14 are filled with air through the connection 40 to the air fill source, rendering the breathing pack 10 ready for use by a firefighter.

(25) In another variant, a high pressure transfer module 402 is provided. The transfer module 402 provides a high pressure connection 274 to a remote pressure gauge console 282, a high pressure connection 406 to the high pressure regulator 46, a high pressure transfer connection 210 for a second firefighter pack (not shown), a low pressure connection 266 to the high pressure regulator 46 for a low pressure hose 54 connected to the low pressure regulator 58 and the mouthpiece 62, a second low pressure connection 202 for use by a second firefighter, and connections for breathing pack electronics 146. The turnout coat 366 has a pocket 410 sized and shaped to removably enclose the high pressure transfer module 402.

(26) In a final variant of the invention, the breathing pack electronics 170 include any of a non-breathing alarm 286, a no motion alarm 290, a two way radio 294, a heads-up display 298 providing air level warning lights 302, and low pressure alarms 306.

The articulated firefighter breathing pack 10 has been described with reference to particular embodiments. Other modifications and enhancements can be made without departing from the spirit and scope of the claims that follow.

The invention claimed is:

1. An articulated firefighter breathing pack, comprising:

a plurality of polymeric pressure vessels, each of said vessels having an elongated cylindrical shape, a first end and a second end;

each of said first and second ends having an attached section of flexible conduit;

each of said sections of flexible conduit being attached to either of a sealing fitting, another section of flexible conduit attached to another vessel and a manifold;

each of said pressure vessels being attached to at least one other pressure vessel with one of said sections of flexible conduit;

said pressure vessels and said sections of flexible conduit being encased in high strength fiber material;

said pressure vessels being wrapped with a high strength ballistic ribbon material;

a manifold, said manifold connected to a plurality of sections of flexible conduit connected to said pressure vessels, and providing connections for a high pressure regulator and an air fill source;

a high pressure regulator, a low pressure hose connected to said high pressure regulator, a low pressure regulator connected to said low pressure hose and a mouthpiece connected to said low pressure regulator;

a pressure vessel container, said container being formed of flexible material, fireproof material and being sized and shaped to accommodate said plurality of pressure vessels, said sections of flexible conduit and said manifold;

said container having a closable opening for introduction and removal of said pressure vessels, said sections of flexible conduit and said manifold and having openings sized and shaped to accommodate passage of at least one low pressure connecting hose and connection to said air fill source;

said container having means for removably attaching to a harness;

a harness, said harness being formed of flexible, fireproof material and comprising a waist portion having a fastener, a front portion extending upwardly from said waist portion and connecting to a back portion extending downwardly to said waist portion, said back portion having means for removably attaching to said pressure vessel container; and wherein said harness is worn over an outer garment of a firefighter, said pressure vessel container is attached to said harness, said manifold is connected to said high pressure regulator, said pressure vessels are filled with air through said connection to said air fill source, rendering said breathing pack ready for use by a firefighter.

2. The articulated firefighter breathing pack, as described in claim 1, further comprising a utility belt, said utility belt having mounting means for accommodating equipment for said breathing pack, a closure means and being worn either of under and over said harness.

3. The articulated firefighter breathing pack, as described in claim 2, wherein said utility belt further comprises a second low pressure hose, a portable power source, breathing pack electronics and mounting means for said high pressure regulator.

4. The articulated firefighter breathing pack, as described in claim 1, wherein said back portion of said harness provides mounting means for accommodating equipment for said breathing pack.

5. The articulated firefighter breathing pack, as described in claim 4, wherein said back portion of said harness comprises a flexible mounting plane, a second low pressure hose, a portable power source, breathing pack electronics and mounting means for said high pressure regulator.

6. The articulated firefighter breathing pack, as described in claim 1, wherein said high strength fiber material is selected from the group consisting of: rayon, nylon, glass or Kevlar® (aramid) fiber.

7. The articulated firefighter breathing pack, as described in claim 1, wherein said high strength ballistic ribbon material is selected from the group consisting of: prepreg carbon fiber or prepreg glass fiber.

8. The articulated firefighter breathing pack, as described in claim 1, wherein said manifold comprises a strip of flexible material, said strip mounting a plurality of connections for said sections of flexible conduit connected to said pressure vessels, a connection for said high pressure regulator and said connection for said air fill source, said flexible strip permitting said manifold to conform to a back of a firefighter.

9. The articulated firefighter breathing pack, as described in claim 1 wherein, said manifold further comprises an integral high pressure regulator.

10. The articulated firefighter breathing pack, as described in claim 1, wherein said high pressure regulator further comprises a second connection for a low pressure hose, said second connection providing an emergency air source for a second firefighter.

11. The articulated firefighter breathing pack, as described in claim 1, wherein said high pressure regulator further comprises a high pressure transfer port, said high pressure transfer port providing an emergency air sharing facility for a second firefighter.

12. The articulated firefighter breathing pack, as described in claim 1, wherein said pressure vessel container further comprises a closable side opening, said side opening extending from a top end of said container to a point spaced from a bottom end by a first predetermined distance, leaving an unopened side portion, said unopened side portion preventing said pressure vessels and said manifold from falling out of said container should it be left open.

13. The articulated firefighter breathing pack, as described in claim 1, wherein said high pressure regulator is a high pressure transfer block, said high pressure transfer block having a pressure gauge, a fill port with shut off valve, a high pressure connection to said manifold, a high pressure transfer connection for a second firefighter pack, a low pressure connection for a low pressure hose connected to a low pressure regulator and mouthpiece, a second low pressure connection for use by a second firefighter, a high pressure connection for a high pressure hose connected to a remote pressure gauge console, and connections for breathing pack electronics.

14. The articulated firefighter breathing pack, as described in claim 3, wherein said breathing pack electronics include any of a non-breathing alarm, a no motion alarm, a two way radio, a heads-up display providing air level warning lights, and low pressure alarms.

15. The articulated firefighter breathing pack, as described in claim 5, wherein said breathing pack electronics include any of a non-breathing alarm, a no motion alarm, a two way radio, a heads-up display providing air level warning lights, and low pressure alarms.

16. The articulated firefighter breathing pack, as described in claim 1, further comprising a remote pressure gauge console, said remote pressure gauge console comprising an air pressure gauge and alarm activation indicators.

17. The articulated firefighter breathing pack, as described in claim 1, further comprising an air pressure gauge, said gauge mounted to said manifold.

18. The articulated firefighter breathing pack, as described in claim 1, wherein said manifold further includes an overpressure rupture fitting.

19. The articulated firefighter breathing pack, as described in claim 1, wherein each of said pressure vessels includes an overpressure rupture fitting.

20. The articulated firefighter breathing pack, as described in claim 1, wherein said polymeric pressure vessels are formed as seamless cylindrical bodies having semi-spherical ends, each of said ends having a central opening connected to said sections of flexible conduit.

21. The articulated firefighter breathing pack, as described in claim 1, wherein said polymeric pressure vessels are formed as a pair of two part shells, said shells being welded together and reinforced with a two part ring assembly.

22. The articulated firefighter breathing pack, as described in claim 1, further comprising a fireproof cover for said pressure vessels.

23. The articulated firefighter breathing pack, as described in claim 22, wherein said fireproof cover further comprises a pair of mating cover halves, said halves being hingedly attached at a first side edge and detachably fastened at a second side edge.

24. An articulated firefighter breathing pack, comprising:

a plurality of polymeric pressure vessels, each of said vessels having an elongated cylindrical shape, a first end and a second end;

each of said first and second ends having an attached section of flexible conduit;

each of said sections of flexible conduit being attached to either of a sealing fitting, another section of flexible conduit attached to another vessel and a manifold;

each of said pressure vessels being attached to at least one other pressure vessel with one of said sections of flexible conduit;

said pressure vessels and said sections of flexible conduit being encased in high strength fiber material;

said pressure vessels being wrapped with a high strength ballistic ribbon material;

a manifold, said manifold connected to a plurality of sections of flexible conduit connected to said pressure vessels, and providing connections for a high pressure regulator and an air fill source;

a high pressure regulator, a low pressure hose connected to said high pressure regulator, a low pressure regulator connected to said low pressure hose and a mouthpiece connected to said low pressure regulator;

a firefighter turnout coat, said turnout coat being formed of flexible, fireproof material and having a rear pocket, said rear pocket sized and shaped to accommodate said plurality of pressure vessels, said sections of flexible conduit and said manifold;

said rear pocket having a closable upper opening for introduction and removal of said plurality of pressure vessels, said sections of flexible conduit and said manifold and having lower openings for said connections for said high pressure regulator and said air fill source;

said turnout coat having front pockets, said front pockets being sized and shaped to contain said high pressure regulator, a portable power source, breathing pack electronics;

a front panel of said turnout coat having a mounting point for a gauge console;

wherein said plurality of pressure vessels, said sections of flexible conduit and said manifold are placed into said rear pocket of said turnout coat, said manifold is connected to said high pressure regulator, said pressure vessels are filled with air through said connection to said air fill source, rendering said breathing pack ready for use by a firefighter.

25. The articulated firefighter breathing pack, as described in claim 24, further comprising:

a high pressure transfer module, said transfer module providing a high pressure connection to a remote pressure gauge console, a high pressure connection to said high pressure regulator, a high pressure transfer connection for a second firefighter pack, a low pressure connection to said high pressure regulator for a low pressure hose connected to said low pressure regulator and said mouthpiece, a second low pressure connection for use by a second firefighter, and connections for breathing pack electronics; and said turnout coat having a pocket sized and shaped to removably enclose said high pressure transfer module.

26. The articulated firefighter breathing pack, as described in claim 25, wherein said breathing pack electronics include any of a non-breathing alarm, a no motion alarm, a two way radio, a heads-up display providing air level warning lights, and low pressure alarms.

* * * * *

UNITED STATES PATENT AND TRADEMARK OFFICE

CERTIFICATE OF CORRECTION

PATENT NO. : 8,251,064 B2
APPLICATION NO. : 12/707287
DATED : August 28, 2012
INVENTOR(S) : Stan A. Sanders It is certified that error appears in the above-identified patent and that said Letters Patent is hereby corrected as shown below:

First Page Column 2 (57) Abstract, line 8, "low" should read --high--.
First Page Column 2 (57) Abstract, line 9, "low" should read --high--.
Column 3, line 12, "low" should read --high--.
Column 3, line 14, "low" should read --high--.
Column 5, line 8, "low" should read --high--.
Column 5, line 10, "low" should read --high--.
Column 5, line 55, "low" should read --high--.
Column 5, line 66, "low" should read --high--.
Column 6, line 65, "low" should read --high--.
Column 6, line 67, "low" should read --high--.
Column 9, line 14, "low" should read --high--.
Column 9, line 17, "low" should read --high--.
Column 10, line 18, "low" should read --high--.
Column 10, line 20, "low" should read --high--.
Column 12, line 41, "low" should read --high--.
Column 12, line 43, "low" should read --high--.

Signed and Sealed this
Sixth Day of November, 2012

David J. Kappos

David J. Kappos
*Director of the United States Patent and Trademark Office*